United States Patent [19]

Aroonsakul

[11] Patent Number: 4,898,857
[45] Date of Patent: Feb. 6, 1990

[54] TREATING CONTROL NERVOUS SYSTEM DISEASES

[76] Inventor: Chaovanee Aroonsakul, 6907 S. Constance, Chicago, Ill. 60649

[21] Appl. No.: 293,132

[22] Filed: Feb. 3, 1989

Related U.S. Application Data

[63] Continuation of Ser. No. 156,242, Feb. 16, 1988, which is a continuation-in-part of Ser. No. 666,254, Oct. 29, 1984, Pat. No. 4,791,099, and Ser. No. 852,645, Apr. 16, 1986, Pat. No. 4,727,041.

[51] Int. Cl.$^4$ ............................................. A61K 31/56
[52] U.S. Cl. .................... 514/171; 514/178; 514/182; 514/879
[58] Field of Search ............... 514/2, 171, 178, 182, 514/879; 424/108

[56] References Cited

U.S. PATENT DOCUMENTS 3,274,060 9/1966 Bossinger ........................... 514/893
4,746,674 5/1988 Pierpaoli et al. ..................... 514/415

OTHER PUBLICATIONS

Cotzias et al CA 86:50823s (1977).
Hagino CA 95:3943g (1981).
Fillit et al Biosis 83:5821o (1986).

*Primary Examiner*—Stanley J. Friedman

[57] ABSTRACT

A method of treating humans suffering from central nervous system diseases, such as Alzheimer's disease, Parkinson's disease, senile dementia. The treatment consists of inducing into the patient's blood stream at least one from the group consisting of: sex hormones and anabolic hormones. Growth hormone is also be used in those patients in advanced stages of the disease, or in those patients where it has been determined that a low level of growth hormone is present. A method of diagnosing Alzheimer's disease, senile dementia, by the determination of the levels of the hormones somatotropin (human growth hormone) and somatomedin-C (IGF-I) after the administration of the Aroonsakul-Allen provocative test is also disclosed. Blood-sera samples are taken at certain time periods after the administration of L-Dopa, and the samples are tested for the levels of these hormones. These levels are then compared against the levels for normal subjects.

3 Claims, 2 Drawing Sheets

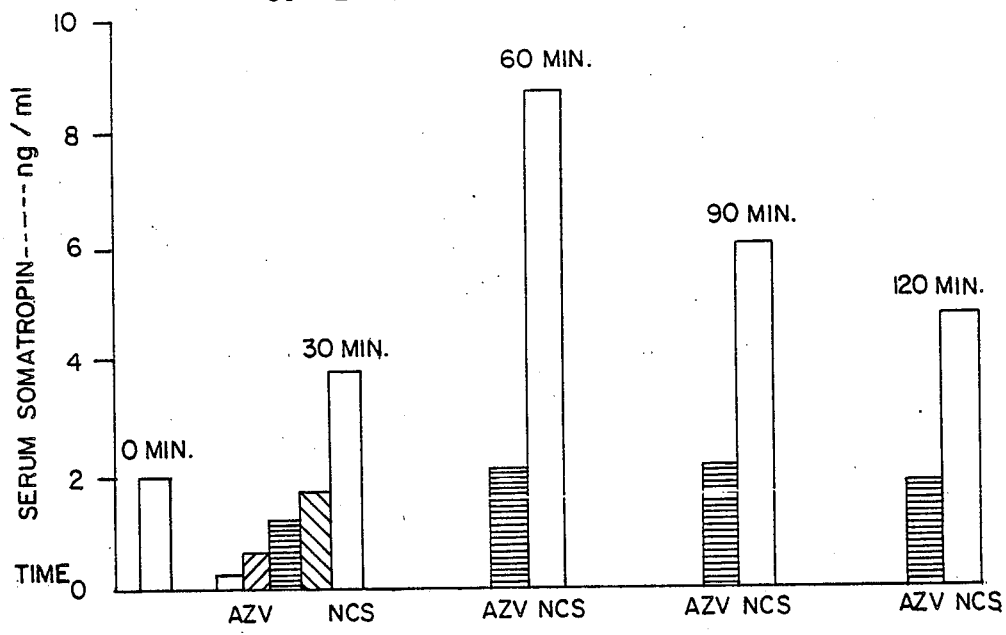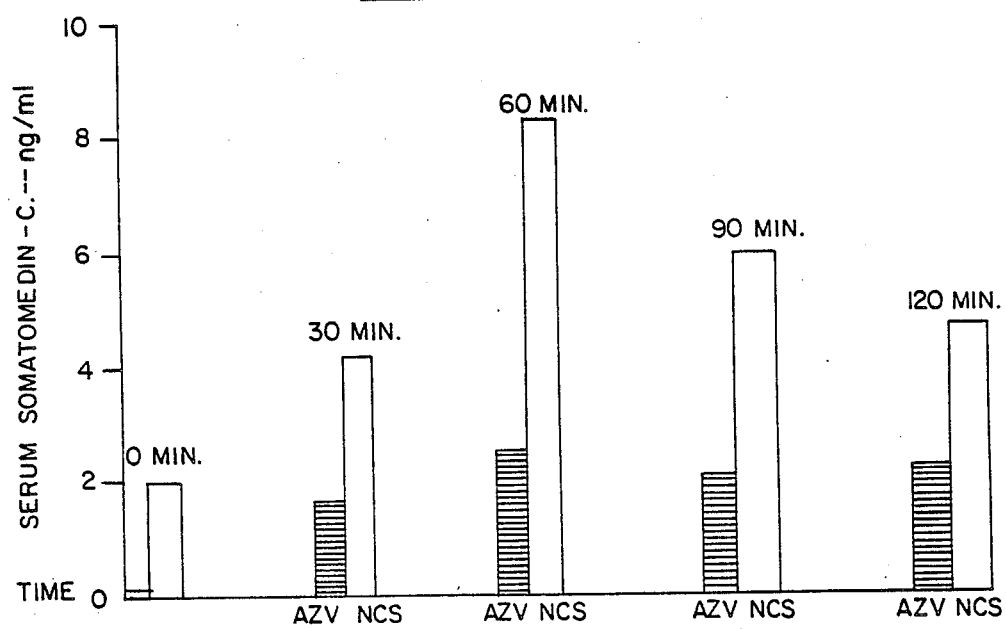

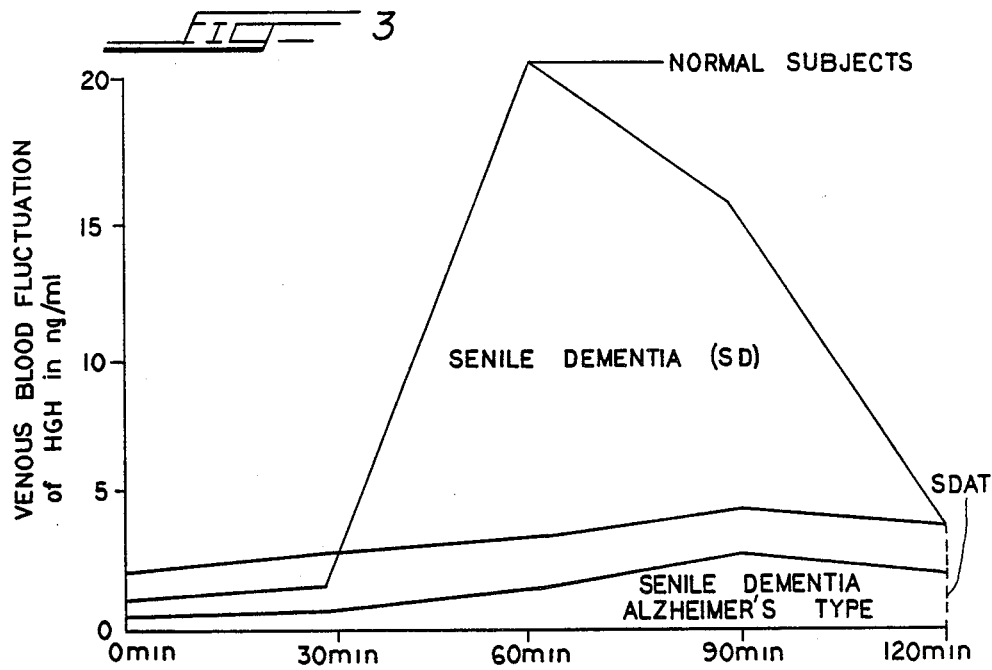
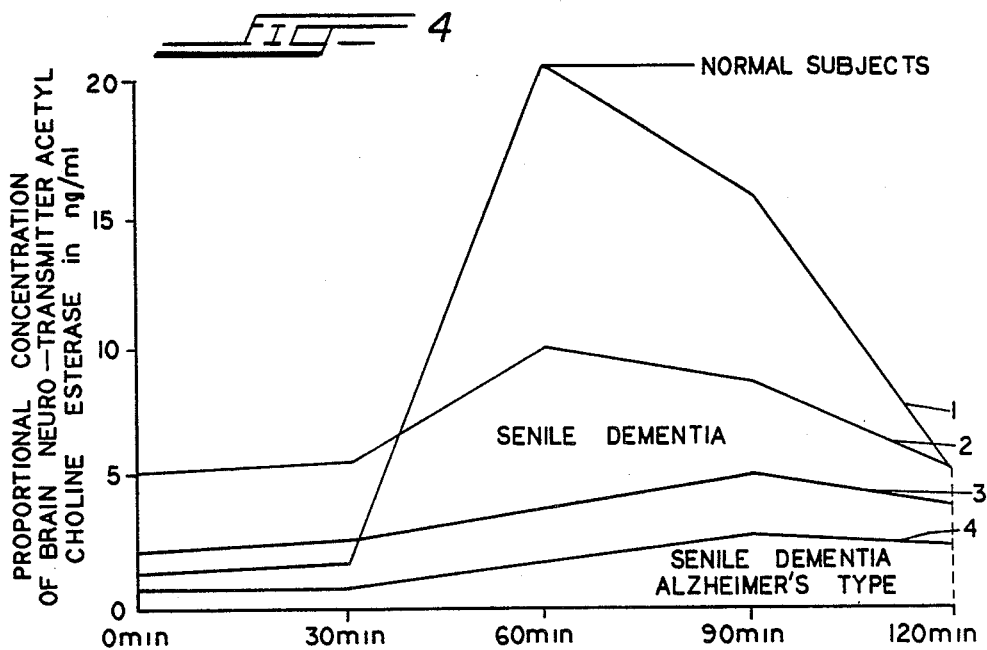

TREATING CONTROL NERVOUS SYSTEM DISEASES

CROSS-REFERENCE TO RELATED APPLICATIONS

This is a continuation of co-pending application Ser. No. 156,242, filed on Feb. 16, 1988 which application is a continuation-in-part of Applicant's co-pending application Ser. No. 666,254, filed Oct. 28, 1984, now U.S. Pat. No. 4,791,099, and Applicant's co-pending application Ser. No. 852,645, filed Apr. 16, 1986, now U.S. Pat. No. 4,727,041.

BACKGROUND OF THE INVENTION

The present invention is directed to a method of treatment for central nervous system diseases. These diseases for which the present inventive method has been found useful are: Alzheimer's disease; Parkinson's disease; senile dementia; essential tremor; senile tremor; and cerebellar atrophy and cerebral atrophy; multiple sclerosis; cerebrovascular accident. Each of these has been found to affect different portions of the brain. Alzheimer's disease affects the portion of the brain vital to memory retention, the cortex. Parkinson's disease is known to affect the nerve cells of the basal ganglia. Cerebellar atrophy is known to affect the nerve cells of the cerebellum. It has also been determined that in each of the above diseases, intrinsic depression develops, which is usually associated with an entirely different portion of the brain than those affected by the above-named diseases. It is also known that in each of these diseases characterized by biochemical lesions in enzymes, membranes, or structure proteins of particular components, cellular atrophy is the result, which is a slow process of cellular deterioration, sometimes deferred bes, but leading to cellular atrophy, and eventually resulting in serious functional loss, causing the symptoms associated with each of the diseases. Such cellular atrophy generally occurs with advancing age, but, owing to these diseases, the processes are somehow speeded up, in a manner not known or understood at the present time. What is certain, however, is that in any cellular breakdown, the enzymes required for protein synthesis are lacking. Further, it is also apparent that this lack of enzyme formation, and concomitant lack of protein synthesis, are caused by some interruption in the neural network through which biochemical signals are generated and transported. Thus, the very problem of each of these diseases runs to the basic structure of life: To wit, RNA and DNA, ribo nucleic acid and deoxyribonucleic acid, which program each cell to provide the necessary enzymes for life-sustaining activity.

Heretofore, there has been no effective method of treatment of each of the above-named diseases. In the case of Parkinson's disease, L-Dopa has been employed and has achieved some success. However, the period of efficacy of L-Dopa is limited to a few months. In the case of Alzheimer's disease, and the remainder of the above-named diseases, ergoloid myselates have been used to some small success.

The present invention is also directed to a method of diagnosing Alzheimer's Disease in human beings. Presently-used techniques for determining Alxheimer's disease include neuropsychological testing which compares the mental status of the patient relative to a norm, as well as the patient's cognitive dysfunction. Such testing also tests for mood depressions, agitation, irritability, and the like, all of which are symptoms of Alzheimer's disease. Other diagnostic tools and methods are: The use of a brain atlas beam test or EEG (electroencephalogram) which demonstrate increases in delta and theta waves. It is, of course, most important that a correct diagnosis be determined in order to decide upon the best treatment. The present invention is directed towards the incorporation of a novel diagnosis for Alzheimer's disease and senile dementia, that may be used in conjunction with other standard testing methods, or may be used alone for such determination, since this novel diagnosis has been found to be very accurate, especially when used in conjunction with conventional diagnostic tests for other chronic degenerative diseases of the CNS form which similar indications may result.

It has been known that the drug levodopa (L-Dopa), a common drug for treating Parkinson's disease, causes increased secretion of the growth hormone somatotropin (HGH-human growth hormone). This finding of Aroonsakul and Allen provocative test (AA provocative test) such as L-Dopa's provocative stimulation of the pituitary gland to secrete HGH was used as the basis for viewing the functioning of the peripheral nervous system (PNS) as an aminergic neuronetwork. Furthermore, since the hormone somatomedin-C (often referred to as IGF-I, for insulin-like growth factor) is directly dependent upon the secretion of HGH by the pituitary gland, there has been established a direct linkage between increased secretion of HGH and increased production of the hormone somatomedin-C, which is produced chiefly in the liver and kidneys. The use of L-Dopa to markedly increase the secretions of somatotropin and, consequently, the production of somatomedin-C in the human body has led to what is generally termed the "L-Dopa provocative test". This test is used to determine the normal functioning of the anterior region of the pituitary gland responsible for the HGH production. Generally, the AA provocative test is used by detecting the increase of HGH and IGF-I in a blood serum by the use of radioimmunoassy (RIA), which determines the presence or absence or the amounts of a certain hormone in a serum by the use of a radioactive agent, used in vitro. RIA involves separation of the labelled antigen that is of interest into bound-unbound fractions after the interaction with an antibody in the presence of the unknown quantity of unlabelled antigen to be measured. The radioactive element used in this determination is usually I-125.

Somatotropin is a growth hormone (polypeptic-link amino acid in character), secreted by the anterior region of the pituitary gland. This is also known as the human growth hormone (HGH), and is the precursor of the hormone somatomedin-C (IGF-I), produced by the liver and kidneys. According to the present invention, it has been discovered that patients suffering from Alzheimer's disease have a deficiency of somatotropin production which leads to a deficiency of somatomedin-C levels, and that exogenous stimulation by a drug to cause increased secretions of HGH in normal human subjects, does not function normally in Alzheimer's patients. Though it has been known to have increased levels of IGF-I in the blood with reduced levels of HGH, these instances are rare and can be taken into consideration when determining the diagnosis according to the present invention.

SUMMARY OF THE INVENTION

The present invention consists of a method of treating patients suffering from the above-named diseases with the hormones: sex hormones and anabolic hormones. For male patients, androgens are used, or suitable anabolic hormone substitutes are used. For female patients estrogens are used in combination with androgens or anabolic hormones Nonsteroidal anti-inflammatory drugs and vasodilaters may be used in combination with the hormone treatment to ensure that the blood delivers the hormone or hormones to the brain. Further, the hormone method of treatment may be supplemented with growth hormones alone or in combination, which are known for their anabolic tendencies, especially in those cases where there has been detected a noticeable loss of such growth hormone in the patient's system, which growth hormones also exhibit remarkable rejuvenating properties.

It is a primary objective of the present invention to provide a novel diagnostic technique and method by which positive identification of Alzheimer's disease in a human being may be established definitively.

It is also an objective of the present invention to use any dopaminergic drug, catecholamine, serotonin, amphetamine, causing immediate excess secretion of the hormones HGH and IGF-I, as well as any drug creating the same excess secretion.

BRIEF DESCRIPTION OF THE DRAWING

The invention will be more readily understood with reference to the accompanying drawing, wherein:

FIG. 1 is a bar-chart showing the levels of the hormone somatotropin in blood sera at the end of specified periods obtained from the results of the L-Dopa AA provocative test;

FIG. 2 is a bar-chart similar to FIG. 1 for the hormone somatomedin-C;

FIG. 3 is graph showing the comparison between the human growth hormone levels of a group of normal subjects as well as the graphs for those diagnosed as suffering from Alzheimer's disease and senile dementia;

FIG. 4 is a graph showing the levels of brain neurotransmitter, acetylcholineesterase, present in blood samples according to the method of diagnosing of the present invention.

DETAILED DESCRIPTION OF THE INVENTION

To reverse the degenerative nature of central nervous disorder disease, such as Parkinson's disease, Senile Dementia, Alzheimer's disease, senile tremor, and the like, and diseases especially associated with dementia, it has been discovered that treatment methods utilizing the synthesizing, metabolic effects of androgens, estrogens, and anabolic hormones have reversed the degenerative nature of the diseases, and have restored patients suffering from the diseases to more normal and productive lives, with the alleviation of many of the symptoms of the diseases. Further, upon continual and prolonged treatment with the above-named group of hormones, there has not been found any diminution of efficacy of the treatment, nor any serious contraindications and adverse side effects.

In one patient suffering from diagnosed Alzheimer's disease and early stage Parkinson's disease, which patient was sixty years old and weighed one-hundred eighty pounds, he was given 10 mg. of fluoxymesterone USP daily. In conjunction with the fluoxymesterone, the patient was given 1 mg. of ergolid myselates four times a day; 50 mg. of dipyridamole, four times a day; and acetyl salicylic acid enteric coated, four times a day, all taken orally. Within one week of the start of this treatment, the patient experienced noticeable improvement, including the cessation of Parkinsonism tremor, and a wider span of attentiveness. In about one month from the start of the treatment, the patient stopped bed-wetting, and was able to concentrate on television, and other mentally-stimulating activities. Within about two months, the patient's intellectual capacity increased so that he could carry on a conversation with another person. Within about three months, the patient was able to dress himself, and take a bath by himself. Within about four months, the patient was able to smile, and laugh occasionally. Within about five months, the patient was able to retain in his memory recent occurrences and happenings. When the above-described treatment and medicine was eliminated, the patient regressed. After resumption of the treatment with fluoxymesterone, with the other drugs above-named, and in their previously given doses, the patient again responded and started to recover from the degenerative nature of the diseases.

In the treatment of central nervous system disorders, and especially those where dementia is present, it has been found that treating patients with the following hormones has caused alleviation of the degenerative nature of the diseases, and has resulted in putting the patient back on the road toward normalcy. These hormones belong to the group: Androgens for male patients; androgen-estrogen combination for female patients; anabolic hormones for either male or female patients; or a combination of any of the three classes within this group.

In the above-cited case history of one male patient who was treated with the synthetic androgen and chorionic gonadotropin, any of the following other androgens could have been used in lieu of, or in conjunction with, the fluoxymesterone; Testesterone; methyltesterone; and oxymethone. Furthermore, the patient could have been treated with any of the following anabolic hormones in lieu of the androgen, or in combination therewith: Oxymetholone; oxandrolone; ethylestrenol; stanozolol; nandolone; phenpropionate; decanoate; and methandriol. Whereas in the case of using the fluoxymesterone, a daily dosage of 10 mg. was provided the patient, in the case of the use of other androgens, either singly or in combination with another androgen, the precise dose could vary. However, it has been found that a minimum dose of 1 mg. of any type of androgen above-named is preferred. Below such level, the beneficial results above-noted would likely not occur.

Further, combinations of anabolic hormones alone, or anabolic hormones with androgens, may also be used to find the precisely-desired anabolic effect to be had on the central nervous system of the patient, again with the minimum daily dosage of 1 mg., either for combinations, or individually-administered hormones.

Since a patient suffering from the diseases of the central nervous system, for which the treatment of the present invention has proven successful, also suffers from other ailments, either because these diseases strike primarily those advanced in age or because of other factors, it has been found necessary to also treat the patient with other drugs in order to ensure that the hormone used is adequately and safely delivered into the blood stream of the patient, and to the site in the brain affected by the disease, so as to act on the degenerative nerve cells. Toward this end, as shown by the above-cited case, the patient is typically treated also with vasodilater and non-steroidal anti-inflammatory drugs, to ensure that the hormone is delivered to the brain. Further, ergoloid myselates are also used, the use of which for dementia has been known in the art. Among vasodilaters, any of the following group may be used, either singly, or in combination: Dipyridamole; cyclospasmol; nylidinhydrochloride; papavarine hydrochloride; and isoxsuprine hydrochloride. Further, any well-known vasodilater may be used, the above being given only by way of example. For non-steroidal anti-imflammatory drugs, any of the following may be used singly or in combination: Aspirin; ibuprofen, indomethacin; tolmetin sodium; and piroxicam. Also, any other well-known non-steroidal anti-inflammatory drug may be used, the above being given only by way of example.

Patients who are in the late and/or vegetative stages need other medication in addition to the medication mentioned above. For women, estradiol, a major anabolic sex hormone in a female is needed. For men, androgen, a major anabolic sex hormone in a male is needed. Thus, in one case history of a female patient 78 years of age, weighing approximately one-hundred fifty pounds, diagnosed as having Alzheimer's disease, the patient was given the following, orally: 1.25 mg. conjugated estrogen once a day; 10 mg. methyltetosterone once a day; 1 mg. ergoloid myselate USP four times a day; 50 mg. dipyridamole four times a day; and 300 mg. acetyl salicylic acid enteric coated four times day.

The ergolid myselate helps, it is thought in the art, that it will serve to prevent the cell's temporary loss of protein; the dipyridamole increase cerebral blood flow; and the acetyl salicylic acid helps to prevent clots among other beneficial results. Just as in the case of the male patient noted above, this female patient experienced marked and fast rejuvenation, dissipation of dementia, increased mental alertness, and a general vitalization such that many of her Alzheimer disease symptoms by conventional diagnosis; but senile dementia disappeared by new biochemical diagnosis in FIG. 3 and 4.

Besides the use of conjugated estrogen, any estrogen from the following group may be used singly or in combination: Estradiol; estrone; estriol. Further, gonadotropins and chorionic gonadotropins may also be used, singly or in combination. Also, another androgen or an anabolic hormone could have been used successfully instead of the methyltestosterone.

In conjunction with the above-disclosed treatment, in these patients where it has been determined that the level of growth hormone in their system is below normal for their size, sex, and age bracket, the above-administering of drugs is supplemented with a growth hormone to re-establish normal levels thereof in the patients. These growth hormones, also of potent anabolic efficacy, serve to restore body function to a state receptive to treatment of the present invention in those cases where growth hormone levels are deficient. Further, the growth hormone may also be used in those patients having normal levels of old age thereof, if it has been found that treatment with the androgen or anabolic hormones alone or in combination have not adequately provided success. Typically, if, after six months treatment with the present invention, improvement has not been shown, administering of growth hormones should be instituted, e.g. chorionic gonodotropin in combination. In the advanced stages of the diseases, a growth hormone is also used alone at the outset of treatment, since owing to its increased and magnified positive metabolic effect, a greater and more concentrated inducement of nerve cell regeneration is needed as described in the diagnostic method of senile dementia Alzheimer style.

It is also indicated that the method of treatment as described in the present invention is successful for the alleviating of at least some symptoms for most patients in the incipient, beginning or intermediate stages of the above-named diseases because of the following:

1. General increase in cerebral blood flow which enhances oxidation, including the normal metabolism of the brain cells;
2. Decrease of catabolism of protein and amino acids;
3. Enhancement of protein anabolism, leading to increased activity of brain cells, with the concomitant increase in red blood cell production;
4. Increase in the retention of calcium and sodium, which improve the axon-presynaptic-postsynaptic cell transmission;
5. Increase of intercellular protein, which increases the formation of DNA and RNA;
6. The revitalization of the nerve cell body dendrite and axons of the pre-synaptic and post-synaptic cells.

It is, of course, to be understood that the dosage given during the use of the treatment of the present invention is dependent upon the weight, size, age, and the like of the patient being treated. Further, any other well-known and equivalent sex hormone and anabolic hormone may be used in addition to those listed above, as long as the anabolic manifestations thereof are prevalent.

It has also been determined that, for female patients suffering from the above-named central nervous system degenerative diseases, the use of estradiol alone in suitable dosage provides sufficient anabolic effect, so that the use of an anabolic hormone supplemental to the female sex hormone is not needed. Estradiol has ample anabolic effect itself to preclude the need of the additional use of an androgen or anabolic hormone. The same holds true for the female gonadotropic sex hormones. Since gonadotropic sex hormones offer potent anabolic effects as well, the use of an androgen and/or anabolic hormone is not needed. However, owing to the relative lack of anabolic effect of conjugated estrogens and estrones, then androgen and/or anabolic hormone would be required in a female patient, when treating her with either a conjugated estrogen or estrone sex hormone. In advanced stages of the above-named degenerative diseases, the use of a gonadotropic female sex hormone is desirable, either alone or in combination with a growth hormone or somatropin alone. The dosage, of course, will vary depending upon the age, size, and weight of the patient. The amount of initial dosage of gonadotropic hormone and chorionic gonadotropic hormone preferably is that dosage presently-used to treat men and women having low levels of sex anabolic hormones. Since use of all of the above hormones causes increased production of human growth hormone, the mechanism by which the method of the present invention is efficacious, human growth hormone should be used alone when the patient lacks the power to create HGH on his own.

In order to properly diagnose Alzheimer's disease, it has been discovered that patients suffering from this disease show a depletion of the human growth hormone somatotropin (HGH) and the HGH-dependent hormone somatomedin-C (IGH-I) which makes connective tissue, die on skin and joints. The growth hormone is secreted by the pituitary gland, while somatomedin-C is secreted mainly by the liver and kidneys by stimulation of somatotropin. This discovery of the lack of proper levels of these two hormones, in combination with the fact that Alzheimer's patients lack the capabilities of producing these hormones endogenously even when exogenous stimuli are created in the body of the patient, has led to the method of diagnosis of the present invention. According to the present invention, the L-Dopa provocative test of Aroonsakul and Allen is used to cause increased secretions of these two hormones, or somatropin alone, in order to determine if the pituitary gland, and the liver and kidneys, are capable of producing these hormones in response to this provocative test. It is important that not only the absolute levels of these two hormones in the peripheral blood serum be tested before the L-Dopa provocative test of Aroonsakul and Allen but also the levels of the increase, if any, produced by the L-Dopa provocative test, in order to determine the current stimulation-capabilities of the peripheral nervous system and the hypothalamus, a well as the beta-adrenergic, alph adrenergic, and dopaminergic control systems. It is believed that the dominant control system is the dopaminergic, which is why L-Dopa causes increased secretions of HGH. For example clonidine propenolol, serotonin, ergoloid myselate causes andrenergic stimulation of the brain which will increase HGH.

The secretion of somatotropin by the pituitary gland is dependant upon many factors, some of them being wellknown, such as physical exercise, physical and hypoglycemic stresses, low-protein intake and others. Endogenous triggers of HGH release include sleep. Whether exogenous or endogenous, the changes in the secretion of the growth hormone (somatotropin) by the pituitary gland are directly dependent upon by the hormone "growth-hormone releasing-hormone" (GHRH) produced by the hypothalamus, which acts directly upon the pituitary gland in order to cause increase secretion of HGH. Exogenous injection of GHRH into the blood system will result in direct increased secretion of HGH. The secretion of HGH, in turn, causes the increased secretion of somatomedin-C by the liver and kidneys, which somatomedin-C is also used as a feedback loop to the hypothalamus to regulate the secretion of GHRH and, thus, the secretion of HGH. The secretion of HGH is also inhibited by the hormone somatostatin, a cyclic peptide having fourteen amino acids, produced by the pancreas. Somatostatin also acts in a feedback loop with the hypothalamus to inhibit production of GHRH and HGH.

It has been the discovery, according to the present invention that patients suffering from Alzheimer's disease lack proper and normal levels of HGH and somatomedin-C, and also lack the capabilities of producing increased amounts of these hormones in response to exogenous stimuli that tend to cause substantially large and immediate increases of secretions in these two hormones, such as occurs during the Aroonsokul-Allen provocative test (dopomine, catecholamine, serotonin). It is the method of the present invention to use the L-Dopa provocative test to cause sudden and substantial increases in the secretions of the hormones HGH and somatomedin-C. By using radioimmunoassay techniques for detecting the levels of these hormones in the blood serum at chosen time intervals, the results therof may be compared with the norm for the age of the patient, to thereby guage if the pituitary gland is capable of reacting to this stimuli to increase production of HGH, so that a firm diagnosis of Alzheimer's disease may be made.

According to the method of the present invention for diagnosing Alzheimer's disease, one day prior to the use of the Aroonsokul-Allen provocative test provocative test, a dosage of 8 mg. og L-dopa per kilogram-of-weight of the patient is administered to the patient in order to activate the HGH-secreting capabilities of the pituitary gland. On the next day, after an overnight fast, the L-dopa provocative test is given, with a dosage of 15 mg. of -dopa per kilogram-of-weight of the patient. A blood sample is taken just prior to the dosage of 8 mg. of L-dopa per kg. on the day prior to the L-Dopa provocative test, and blood samples are also taken immediately before the start of the L-Dopa provocative testing, and every 30 minutes after the dosage of 15 mg./kg. has been administered. Each blood serum is then tested by RIA techniques to determine the absolute levels of somatotropin and somatomedin-C, and compared against the normal values for the age of the patient being tested. Referring to FIG. 1, there is shown a bar-chart comparing the levels of somatotropin and somatomedin-C obtained by RIA techniques for the five blood sera taken during the provocative test with the levels for normal subjects aged fifty and over. The shaded bars represent typical levels of a patient who has Alzheimer's disease, while the unshaded bars indicate the levels for a normal person aged fifty and over, for the five sera assayed. As it may be seen, for normal subjects, the readings at times: 0 minutes, 30 minutes, 60 minutes, 90 minutes, and 120 minutes are, approximately: 2.00 ng/ml; 3.75 ng/ml; 7.90 ng/ml; 6.05 ng/ml; and 4.45 ng/ml. For patients suffering from Alzheimer's disease the corresponding values are, approximately: 0.02 ng/ml; between 0.03 ng/ml and 1.85 ng/ml; 2.15 ng/ml; 2.05 ng/ml; and 1.85 ng/ml. The values indicated for the normal subjects are the statistical mean average The highest value shown in FIG. 1, for a patient suffering from Alzheimer's disease, for each of the sera tested by RIA is that lying outside of the standard statistical error associated with the RIA testing.

FIG. 2 shows similar results for the RIA of the hormone somatomedin-C. For normal subjects age 50 and over, the values from RIA of this hormone are approximately: 1.95 ng/ml; 4.00 ng/ml; 8.05 ng/ml; 5.90 ng/ml; and 4.45 mg/ml. The corresponding values of Alzheimer's disease patients, are approximately: 0.10 ng/ml; 1.65 ng/ml; 2.15 ng/ml; 2.00 ng/ml; and 2.05 ng/ml.

It is, of course, possible to use different time periods in which the blood sera are taken for subsequent RIA analysis, with these results being compared to a standard for subjects aged 50 and over for the same time periods tested. According to the present invention, substantial differences in levels of these two hormones during the AA provocative test as compared with the normal subjects is a positive and definitive indication of Alzheimer's disease. Furthermore, the absolute differences between the tested sera and the levels for normal subjects may also be used for an indication as to the state of advancement of Alzheimer's disease in the patient. Tested levels far outside the statistical norm adjusted for standard statistical error would mean a more advanced stage of the disease.

There will be some instances where the levels of somatotropin will increase and be similar to those of normal subjects, but the levels of somatomedin-C will fall far short of those for normal subjects, as could occur if the patient were suffering from liver disease. Thus, the AA provocative test would show a mixed result. In this case, further testing would be required, and a positive determination of Alzheimer's disease would have to be confirmed in conjunction with other, currently-used, prior art methods of diagnosis, such as EEG testing, neuropsychological testing, and the like. Also, where the results from the AA provocate test do not show enough differences between the patient being tested and the norm, such as might occur if the values determined by RIA were not outside the statistical mean error of the normal group, then these other conventional methods of diagnosis would be used in conjunction with the method of the present invention. Whereas, both HGH and IGF-I deficiency in children may occur, as in dwarfism, such matched deficiency in adults is not known to indicate any other disease but that discovered according to the present invention. Since during basal, morning conditions there usually cannot be detected any differences between normal subjects and those with HGH deficiency, the provocative test is required, as described above.

Any other HGH-provocative agent may be used instead of L-Dopa. For example, bromocriptine, propanolol, serotonin, catecholamine clonidine, other dopaminergic stimuli, and glucagon, a small peptide that mediates the flow of glucose to insulin-independent tissues. course, the time periods between which the blood sera are taken will depend upon the somatotropin-provocative agent used. Other constraints and conditions will, of course, change dependent upon the HGH-provocative used, and will be obvious to one having ordinary skill in the art. For example, for glucagon as the HGH-provocative, overnight fasting would not be required.

The same type of provocative test above described may also be used for diagnosing senile dementia in human beings, as shown in FIGS. 3 and 4, which are graphs of the levels of the hormone being detected for the subject patient diagnosed as suffering from Alzheimer's disease or senile dementia as compared to a controlled group thereof. The same method of diagnosing is carried out as above described when using the desired provocative test. It has also been discovered that the detection of the proportion of the brain neurotransmitter, aceylcholineesterase, is also indicative of a diagnosis of Alzheimer's disease or senile dementia, as shown in the graphs of FIG. 4 where the ordinate is time and the abcissa is the proportion of the brain neuro-transmitter, acetylcholineesterase, to the total blood sample for normal subjects and those suffering from Alzheimer's disease or senile dementia. In FIG. 4, the graph labelled 1 shows the readings of the proportion of the bain transmitter acetlycholineestrase for normal subjects, while the graph labelled 2 shows the upward limit of the readings for the proportion of the brain transmitter indicative of Senile Dementia. The graph labelled 4 indicates the readings at or below which is an indication of Alzheimer's Disease. The region between the graphs labelled 3 and 4 is a transition region, readings lying therein not being clearly definitive as to Senile Dementia or Alzheimer's Disease.

The method of treating a patient diagnosed as suffering from Alzheimer's disease or senile dementia via the above-described provocative test and method of diagnosing is determined by the results of that diagnostic method and the calculated deficiency of somatropin in the blood of the patient. The range of somatropin dosages is between 0.015 mg to 0.8 mg. per kilogram of body weight of the patient. Such somatropin replacement may take the form of actual dosages of somatropin, or human growth hormone, (synthetic somatropin may be used) in the case of advanced stages and where the depletion is marked, or may take the form of dosages of testosterone, estradiol, and the other anabolic hormones above-enumerated, which themselves indirectly cause the production of somatropin in the body, to thereby efficaciously treat the disease as above-described in the case of less-advanced stages.

It has also been discovered that dosages of somatropin is effective in treating the following: Chronic degenerative disease of the joints, such as arthritis; hypoplastic anemia in aging; osteoporosis during aging; atrophy of the visceral organs such as the kidneys, liver, spleen during aging; atrophy of muscle tissue during aging. Furthermore, it has been discovered that dosages of somatropin, within the range above-defined, is effective in treating general weakness, lack of energy, slow movement, and is even effectuve in smoothing out wrinkles and eliminating wrinkles altogether in some circumstances.

While specific embodiments of the invention have been shown and described, it is to be understood that numerous changes and modifications thereof may be made without departing from the scope, intent and spirit of the invention as set forth in the appended claims.

What I claim is:

1. A method for treating central nervous system diseases in human beings, which diseases are selected from Senile Dementia, Parkinson's disease, cerebral atrophy, Alzheimer's disease, cerebellar atrophy, senile tremor, and essential tremor, comprising:
   inducing into the blood stream of of a human being suffering from the disease an effective dosage of a group consisting of: androgens.

2. The method according to claim 1, further comprising administering at least one of a gonadotropin and chorionic gonadatropin.

3. The method according to claim 1, wherein said androgens is taken from a group consisting of: testosterone, methyltestosterone, fluoxymesterone, and oxymethone.

* * * * *